United States Patent [19]

Skov et al.

[11] Patent Number: 5,468,650
[45] Date of Patent: Nov. 21, 1995

[54] CLASS MICROFIBER HISTAMINE ASSAY DEVICE

[75] Inventors: Per Stahl Skov, Copenhagen; Ole-Christian Bjarno, Holte, both of Denmark

[73] Assignee: A/S Lundbeck Export Division Ltd., Copenhagen, Denmark

[21] Appl. No.: 203,683

[22] Filed: Feb. 28, 1994

Related U.S. Application Data

[60] Continuation of Ser. No. 816,759, Jan. 2, 1992, abandoned, which is a division of Ser. No. 392,363, Aug. 10, 1989, Pat. No. 5,098,831, which is a continuation-in-part of Ser. No. 258,528, Oct. 17, 1988, Pat. No. 5,041,390.

[51] Int. Cl.⁶ .................. G01N 33/552; G01N 33/543; G01N 33/49
[52] U.S. Cl. .................. 436/527; 436/518; 435/287.1; 435/810; 435/962; 435/7.1; 435/287.9; 435/288.4; 422/57; 422/58; 422/61; 427/180; 427/189; 427/196; 427/215; 427/220
[58] Field of Search .................. 435/7.1, 287, 810, 435/961, 962; 436/523, 527, 169; 422/58, 61; 427/180, 189, 196, 214, 215, 220

[56] References Cited

U.S. PATENT DOCUMENTS

| 4,592,956 | 6/1986 | Gaa et al. | 428/391 |
| 4,794,090 | 12/1988 | Parham et al. | 436/531 |
| 4,869,875 | 9/1989 | Skov et al. | 422/58 |

*Primary Examiner*—Toni R. Scheiner
*Assistant Examiner*—Nancy J. Parsons
*Attorney, Agent, or Firm*—Darby & Darby

[57] ABSTRACT

A histamine diagnostic assay device is provided in which glass microfibers treated with a polar organic polymer are deposited onto a carrier and used to selectively bind histamine in a sample. The polar organic polymer reduces the affinity of the glass microfibers for interfering components of the sample while substantially retaining the histamine-binding capacity. Preferably, the glass microfibers are provided as a conglomerate with the polar organic polymer. An agent which induces the release of histamine from cells in the sample may be included in the device.

14 Claims, 2 Drawing Sheets

CLASS MICROFIBER HISTAMINE ASSAY DEVICE

This is a continuation of application Ser. No. 07/816,759, filed Jan. 2, 1992, now abandoned which is a division of application Ser. No. 07/392,363, filed Aug. 10, 1989, now U.S. Pat. No. 5,098,831; which is a continuation-in-part of application Ser. No. 07/258,528, filed Oct. 17, 1988, now U.S. Pat. No. 5,041,390.

BACKGROUND OF THE INVENTION

1. Field of the Invention

The present invention provides a method and a test set for determining histamine present in samples, in particular whole blood. The method is based on a selective binding of histamine to certain materials, and is useful in the diagnosis of allergy related to specific allergens.

2. Information Disclosure Statement

It is essential for allergic patients to know which of the allergens present in their environment or diet give rise to the allergic reaction. Thus, there is a pressing need for the development of accurate, precise, easily applicable and inexpensive methods for establishing which allergens are relevant for the patient.

Methods based on imitation of the in vivo reaction involve the following:

It is known that allergenicity may be evaluated by exposing certain cells, obtained from the patient, to the allergens considered to be of importance, thus inducing a histamine release from said cells, and subsequent measuring the amount of histamine released.

A method based on this principle is described in U.S. Pat. No. 4,550,085. In its more general aspect, the patent discloses a method for detecting or determining histamine in body fluids which comprises: contacting a sample of the fluid with glass microfibers deposited onto a carrier in such quantitative proportions between the glass microfibers and the fluid as will permit the histamine amount to be detected or determined to be bound to the microfibers; and registering or measuring the bound amount of histamine.

In particular a method for detecting histamine possibly released by allergic reaction in body fluids is disclosed wherein the body fluid is contacted with a test allergen and the possibly released histamine bound to the fibers is registered directly or competitively.

According to the working examples in the above mentioned patent the cell phase contacted with the allergens in question was a specially prepared blood cell suspension, namely a cell suspension enriched with leucocytes. To prepare this suspension, blood was drawn from the patient, and the erythrocytes were sedimented. The leucocyte-enriched plasma layer obtained was carefully transferred to another container, suspended in a buffer, and then centrifuged in order to isolate the leucocytes from the major part of the plasma. The supernatant obtained was removed, and the pelleted leucocytes were resuspended in a buffer. This step was further repeated to yield a cell suspension especially enriched with basophile leucocytes.

Accordingly, the sample contacted with the glass microfiber deposited on the carrier was not whole blood as such, but a blood sample which had been subjected to several intermediate treatments.

Pending U.S. divisional application Ser. No. 791,722 is directed to an analytical agent for use in histamine detection particularly in accordance with the method of U.S. Pat. No. 4,550,085, which comprises individual glass microfibers fixed onto a carrier, said agent adapted for use in the detection or determination of histamine possibly released by allergic reaction in body fluids which further comprises the reversible deposition of at least one test allergen.

Based on the same priority application DK 2982/81 as the U.S. Pat. No. 4,550,085, and international application WO 83/00229 was filed. The only essential difference with relation to the U.S. patent and its divisional application is the provision of a further example representing a preferred embodiment using a microtiter plate as a means for carrying out a direct histamine determination. Based on this international application, a number of patents have been granted, e.g. EP pat. no. 82,862, FI pat. no. 74,818 and AU pat. no. 563,306.

The method according to the above patent family has given rise to a number of articles proving its reliability.

In Agents and Actions, vol. 14, 3/4 (1984), p. 414–416 the histamine test according to application WO 83/02229 is further elucidated. The test was performed on washed blood.

In order to avoid loosing of the microfibres during the various washing steps the crushed glass microfibres were fixed to the bottom of the microtiters plates with a water soluble glue.

In Allergy, vol. 42, (1987), p. 336–373 the method according to WO 83/00229 is applied to compare the microfibre-based histamine analysis with conventional histamine release assays, (e.g. the skin prick test and bronchial provocation test).

The method is reported for samples of blood washed by means of Pipes-AMC buffer in order to avoid trapping of the blood cells into the microfibres.

During studies of radioenzymatic assay for histamine Verburg and Henry, Agents and Actions, vol. 14, 5/6, (1984), p. 633–636 investigated adsorption of histamine by glass surfaces in order to obtain techniques to limit the phenomenon. It was reported that potassium phosphate buffers completely prevent histamine binding, that bovine serum albumin blocked adsorption, but that Tris-buffer at pH 7.8 and $K_2EDTA$ limited adsorption.

According to FR patent no. 1,443,167, C.A. Vol. 66 (1967), p. 4642 agglomeration of mineral fibers, i.e. rock wool, slag wool, glass wool, is known to improve mechanical characteristics and better resistance to moisture by bringing a binder, e.g. a starch paste or PhOH-HCHO-resin, on the fibers and then evaporate the solvent and polymerise the resin. Nothing is said about utilization of such agglomerates for analytical purposes.

The above mentioned prior art, in particular the patent family based on DK application no. 2982/81 is incorporated herein by reference.

SUMMARY OF THE INVENTION

The present invention provides a method for the determination of histamine released by the leucocytes of whole blood, said method permitting direct employment of whole blood without the need for initial isolation/washing steps. For several reasons, it is clearly advantageous to be able to employ whole blood directly, i.e. to contact the blood directly with a compartment containing a histamine release-inducing agent and histamine-binding material;

the omission of various fractionation steps results in increased accuracy and precision of the assay;

time-consuming blood fractionation is avoided and hence the total analysis time is significantly reduced;

the requirement for centrifugation equipment is eliminated;

the risk of contaminating the sample material during fractionation steps is eliminated;

the risk of inducing artificial changes in the histamine release ability of the cells during centrifugation and washing manipulations is eliminated;

the risk of operator contact with any pathogenic agents, such as infectious and/or toxic agents, present in the blood sample is minimized;

the risk of mistaken exchange of samples from different patients is reduced;

the amount of blood necessary for the analysis is reduced.

Despite these reasons for analyzing whole blood samples, allergenicity is presently analyzed using specially processed leukocyte samples. The justification is that whole blood contains various components, notably proteins such as albumin, fibrinogen and hemoglobin, which may interfere with a histamine-binding assay. The present inventors have overcome this problem by contacting the sample with a histamine-binding inorganic material which has been treated to reduce its affinity for interfering components, such as hemoglobin, while its histamine-binding capacity has been substantially retained.

After incubation of the sample with the histamine-binding material, the two are separated and the latter is preferably washed with agents that remove interfering components without significantly affecting the bound histamine. When the histamine-binding material is available in the form of granules, flakes, fibers, etc., it is preferable to conglomerate these discrete bodies using a suitable binder, as the resulting conglomerate will better survive the rigors of the washing step. Thus, in another preferred embodiment, such a conglomerate is used as the histamine binding agent in the contemplated assay, and preferably, treated to also reduce its affinity for interfering components.

Summing up, the present invention has the advantages that

1. The production time of the fiber coated carrier may be reduced.

2. The fibres are more securely fixed to the carrier.

3. The background fluorescense is reduced.

4. The histamine binding is surprisingly improved.

5. The standard deviation on fluorescense detection is reduced.

6. The test may be performed on whole blood plasma, cell suspensions or biopsies, thus improving its utility.

Further aspects of the invention are set forth in the following description and claims.

BRIEF DESCRIPTION OF THE DRAWINGS

FIG. 1 shows a diagrammatic view of a test set according to the invention in the form of a tray comprising wells with histamine-binding glass fibres therein, FIG. 2 shows an enlarged sectional view of one of the wells shown in FIG. 1, FIGS. 3–5 show the steps in the process of tray preparation and treatment.

DETAILED DESCRIPTION OF THE INVENTION

The present invention is particularly related to determining histamine in samples obtained from humans or animals. Especially, the invention relates to the determination of histamine in body fluids. Important examples of body fluids are blood and various other fluids which contain histamine-containing cells and/or cells which release histamine.

Such fluids and other body fluids often contain protein components, which have a tendency to adhere to histamine-binding material, and/or to interfere with the effective binding of histamine to histamine-binding material. These interfering components may either be present in the fluid phase or in cells present in the body fluid samples. In cases where such biological components have a high affinity to the histamine-binding material, in particular histamine-binding inorganic materials, they may tend to build up a phase or physical-chemical barrier which would prevent histamine from properly binding with a histamine-binding material— and/or these components may compete with histamine in the binding to histamine-binding material. Therefore, it is important to employ agents and methods which will counteract the interference from such components. The present invention provides such solutions.

Especially relevant is a modification of the histamine-binding material which modifies the surface of the material in such a manner that binding of biological components other than histamine, otherwise showing a strong adhesion to the surface, is reduced without unduly impairing histamine binding.

The term "whole blood or substantially whole blood" is often used. The term "substantially whole blood" is intended to designate blood samples which retain all of or a considerable proportion of the erythrocytes originally present in blood samples from a patient. Whole blood may either be whole blood as drawn from the patient, or such whole blood which has been slightly modified such as by dilution, as distinct from treatments such as fractionation by centrifugation or other labour-consuming blood fractionation procedures.

Blood may be taken by venipuncture from an individual and collected into suitable containers, e.g. plastic or glass tubes (e.g. "Venoject" tubes). A suitable anticoagulant is preferably present in the container prior to the collection of blood. The anticoagulant is preferably an anticoagulant substantially not interfering with histamine release from the cells in question, e.g. not interfering with components essential to the reactions involved in the release or in the analysis procedure. Heparin, e.g. in the form of sodium or potassium heparinate, is a preferred anticoagulant. Typically 0.5 ml of a 30 U heparin/ml solution is employed so as to obtain 3 U heparin per ml blood when 5 ml blood was collected. Usually 5 ml blood is collected, however 2–3 ml provide enough sample material for testing for allergy to several allergens, e.g. 2.5 ml is used in a tray comprising 96 wells. For testing for allergy to a single allergen, as little as 1 ml of blood is sufficient, including sample and blank.

In the present context the term "inorganic histamine-binding material" designates any material which is capable of binding histamine and which is of either inorganic character or predominantly inorganic character. Examples of such inorganic materials are described in greater detail below, including laboratory-prepared glass types which may contain minor proportions of organic residues but which are in the present context considered inorganic materials.

The term "determination" as used in the present context is normally used to denote measurement of concentration, but in certain instances is used to denote qualitative identification.

The determination of histamine may be performed by any suitable determination method having the necessary sensitivity, such as competitive determination, e.g. involving the use of labeled histamine, or direct determination, e.g. by spectrophotometry.

An example of a procedure for determination of histamine which is employed in a preferred embodiment of a method according to the present invention as exemplified herein is a fluorometric assay procedure. This procedure is based on coupling of histamine with a fluorophore, viz, ortho-phthaldialdehyde, with essentially quantitative formation of a fluorescent ring structure whose concentration can be related to the measured fluorescence intensity. The underlying principle of this assay is described in Hoppe-Seyler's Z. Physiol. Chem. 353, 911–920, 1972.

In a preferred embodiment described herein, histamine is freed from the histamine-binding material at high pH (>10), the high pH also being required for satisfactory reaction between freed histamine and ortho-phthaldialde-hyde (OPT). Perchloric acid is then added to reduce pH to a low value necessary for ensuring adequate stability of the fluorescent reaction product formed between histamine and OPT.

By the term "conglomerate" is meant any physical composite of the histamine-binding material and the binder. The histamine-binding material may be in the form of a body or bodies of relatively macroscopic dimensions; it may also be of more microscopic dimensions, suitably in the form of fibers. Fibers in the present context normally have a length-:diameter ratio of at least 4:1.

When the bodies of histamine-binding material are in the form of fibers, such fibers are advantageously employed in the form of microfibers, for example microfibers formed by comminution of longer fibers. The length of such microfibers is preferably between 0.5 and 100 (or even 200) μm, more preferably from 1 to 50 μm, especially from 1 to 25 μm, in particular 2 to 20 μm: the diameter is preferably between 0.1 and 10 μm, more preferably 0.2 to 5 μm, in particular 0.3 to 2 μm.

The conglomerate may thus comprise fragments of histamine-binding material, for example flakes, pieces of sheet, or lumps of dimensions greater than or equal to several millimeters, wholly or partly covered with the binder. At the other extreme, the conglomerate may comprise microscopic bodies of histamine-binding material of dimensions such as those mentioned above for microfibers, these microscopic bodies being gathered into a mass or coherent whole which is bound together by the binder. This mass or coherent whole may, for example take the form of roughly spherical or more irregularly shaped entities, the individual microscopic bodies of which may or may not be wholly or partially covered by the binder. It may also, as in a preferred embodiment of the present invention, adopt a form dictated by the geometry of a carrier to which the conglomerate is affixed. In the preferred embodiment of the invention, the carrier is the bottom of a well in a polystyrene tray, the conglomerate adopting the form shown diagrammatically in FIG. 1 (vide infra).

The bodies of histamine-binding material may also be in the form of powder or other particles, including porous particles; they may further be, for example, porous and/or fibrous or otherwise subdivided (to obtain a high surface area) domains of otherwise substantially continuous bodies such as sheets (or, e.g., well sides and/or bottoms) which domains have been prepared, e.g., by casting, mechanical, thermal, electrical and/or chemical roughening treatment, e.g. etching, or other means suitable for providing domains with elements of a high surface area.

In the present context the term "carrier" designates any suitable support device to which the conglomerate may suitably be affixed, such as a container or vessel, or microcontainer or microvessel, a tube, or any other kind of solid support to which the conglomerate is suitably affixed for the purpose of the analysis.

It may, for example, be in the form of a micro-scale column comprising a filter capable of supporting the glass bodies, so that the glass bodies can be contacted with a histamine-containing sample and then eluted with relevant reagents or media.

However, also other kinds of carriers or supports are possible, such as bodies which in themselves are not capable of housing any liquid but which are designated for being immersed in a liquid for example beads such as solid or hollow beads, or entities of various shapes in small sizes designated for immersion into a sample.

The carrier preferably consists of a material which is substantially inert under the reaction conditions prevailing during determination, for example a thermoplastic synthetic resin such as polystyrene.

The inorganic histamine-binding material may be either substantially amorphous or substantially crystalline in structure, and may very suitably be a silicon dioxide based material, that is, a material containing a significant amount or a major proportion of silicon dioxide, or made from or formed from a material comprising a significant amount or a major proportion of silicon dioxide. Such a material can, for example, be silicon dioxide based glass materials or quartz.

The term "glass material" as used in the present context denotes a material which is based wholly or partly upon silicon dioxide, and which has a substantially amorphous structure and an extremely high viscosity.

Examples of important types of glass which might be used in the present invention include:

silicon dioxide glass, consisting of amorphous, fused silicon dioxide;

soda-lime glass, consisting typically of a fused homogeneous mixture of silica (ca. 75%), soda ash (ca. 20%) and lime (ca. 5%);

borosilicate glass, which is normally a soda-lime type glass, further containing boric oxide (often ca. 5%).

The glass material of WHATMAN GF/B glass fiber sheet (vide infra) is an example of a typical borosilicate glass.

A number of types of glass of the soda-lime type tailored to meet requirements for specifik properties are also produced by the further incorporation of certain metallic oxides, for example oxides of magnesium, barium, lead, zinc, aluminium, lithium or cerium.

U.S. Pat. No. 4,550,085 discloses advantages associated with the use of glass microfibers prepared from glass microfiber filter sheet marketed under the name of WHAT- MAN GF/B for selectively binding histamine. According to the manufacturer's product information, the borosilicate glass from which these fibers are fashioned is a borosilicate glass of relatively high boric oxide content as can be seen in the following table (Table 1) specifying the typical composition of this glass together with other glass materials which have been tested for histamine-binding properties (vide infra):

TABLE 1

Typical compositions of histamine-binding materials % (w/w)

|  | GF/B | CPG-10 | 106 Q | 108 A |
|---|---|---|---|---|
| $SiO_2$ | 57.9 | >98.0 | 98.5 | 58 |
| $B_2O_3$ | 10.7 | — | — | 11 |
| $Fe_2O_3$ | 5.9 | — | — | — |
| $Al_2O_3$ | 10.1 | — | — | 6 |
| $Na_2O + K_2O$ | 2.9 | — | — | 13 |
| CaO | 2.6 | — | — | 2 |
| MgO | 0.4 | — | — | — |
| BaO | 5.0 | — | — | 5 |
| ZnO | 3.9 | — | — | 4 |
| F | 0.6 | — | — | — |
| Others |  | <1.5 | 1.5 | 1 |

GF/B    Borosilicate Whatman
CPG-10, Controlled Pore Glass Spectrum ®
108 A,  Borosilicate, Tempstran ®
106 Q,  High Silica, Tempstran ®

Selective histamine-binding at a level satisfactory for use in a method according to the present invention is not confined to glass of the borosilicate type in that, e.g. pure silicon dioxide glass, a number of laboratory-prepared glasses of composition similar to glass of the soda-lime type, but without calcium oxide as a component, and a number of laboratory-prepared glasses prepared partly on the basis of metal or non-metal alkoxides as components all appear to exhibit useful histamine-binding properties.

An example of a crystalline silicon dioxide based material is quartz, i.e. pure, crystalline $SiO_2$, which has been found by the present applicant to exhibit histamine-binding properties.

Based upon the disclosure of U.S. Pat. No. 4,550,085, the other members of its patent family and the present disclosure, the person skilled in the art will be able to determine the histamine-binding properties of other types of materials not specifically mentioned here.

In view of the ready commercial availability and reproducibility of WHATMAN GF/B glass microfibers, however, these microfibers are presently preferred as starting material for the preparation of glass microfiber for use in a method according to the invention, an example of a preferred embodiment of the preparation of such glass microfibers from WHATMAN GF/B glass fiber filter sheet being described in detail in Example 1 (vide infra).

In the present context, the term "binder" is intended to designate any substances that is capable of bonding other substances together by surface attachment. In order to avoid confusion it should be mentioned that the term "binder" has previously been used in the U.S. Pat. No. 4,550,085 and its family as designating a "histamine-binding material", since the advantageous proportion of the binder as used in the present context had of course not been realized earlier. Naturally, the binders used according to the present invention should be binders which result in a suitable conglomeration of the histamine-binding bodies while at the same time leaving sufficient access of histamine-containing fluids to the bodies. From a chemical point of view, the binders should be selected so that they do not adversely influence the measured results. The binders may suitably be binders which are synthetic organic polymers and, as they are to bind and retain the conglomerate in-situ during contact with normally water-containing samples, it is preferred that the polymers are substantially water-insoluble although binders which are applied from e.g. an aqueous dispersion are perfectly suitable for the purpose of the present invention provided that they will remain substantially water-insoluble once they have been applied.

As examples of suitable binders may be mentioned polyvinyl esters such as polyvinylacetate or copolymers such as vinyl acetate/ethylene copolymers, optionally in combination with polyvinyl alcohol. As will appear from the following explanation, the latter type of binders may, together with their binding capacity as attachment substance both intraconglomerate and between conglomerate and carrier, show surprising advantages as interference reducing agents with respect to reducing possible interference from body fluid components such as proteins in the sample.

The amount of binder to be applied will depend upon the character of the binder and the histamine-binding bodies. It appears that suitable ranges of binders are from about 0.1 to about 20 percent solid weight, in particular from about 2 to about 10 percent, preferably from about 4 to about 8 percent solid weight of binder, calculated on the basis of the histamine-binding material.

According to a particular and important aspect of the invention, the histamine-binding material is an inorganic material which has been treated to reduce affinity towards interfering components in the samples examined, in particular samples of body fluids (especially samples of whole blood or substantially whole blood or other body fluid samples in which erythrocytes or erythrocyte components/fractions or components of similar interfering character, such as protein components, are present in significant amounts), have been reduced while the histamine-binding capacity of the glass has been substantially retained.

Without being bound to any particular hypothesis, it is believed that the mechanism of reducing the affinity of the inorganic material towards interfering components can be described as a phenomenon associated with the reduction of polarity and/or surface tension of the surface so that the adhesive forces of the inorganic material towards interfering components have been reduced.

As will be understood, an inorganic material, of which the adhesive forces towards proteins e.g. hemoglobin have been reduced will also normally show substantially reduced adhesive forces towards other interfering components in body fluid samples (because hemoglobin can, in many contexts of relevance herein, be considered representative of the interfering substances) and will thus show distinct advantages in the method of the invention.

Therefore, a measure of the usefulness of the treatment of an inorganic material to reduce its adhesive forces towards interfering substances may normally be obtained by ascertaining the behaviour of the treated material towards hemoglobin or a hemoglobin analogue or another related globin such as e.g., myoglobin; a reduction of the adhesive forces towards hemoglobin or hemoglobin analogues or other related globins with retainment of adequate histamine binding is thus an indication of increased utility of a treated inorganic histamine-binding material for the general purposes of the present invention.

While the term "treatment" is used in the present context, it will be understood that the reduced affinity of interference towards an inorganic histamine-binding material may also be obtained by incorporation of interference-reducing e.g.

polarity reducing substances during the production of the inorganic material; in the present specification and claims, this possibility is included in the term "treated" or "treatment", or "prepared".

By the term "affinity of interfering components" is meant that the interfering components have distributions between nthe solid phase and the liquid phase such that they interfere with the histamine binding.

The affinity of interfering components may be of physical as well as chemical nature, and may be described in terms of the polarities of the solid and liquid phases, respectively, or in terms of surface tension for apolar substances as mentioned previously.

A reduction of the polarity and/or surface tension of the surface of a histamine-binding inorganic material (glass being used as an example thereof in the following explanation) may be obtained by treatment with a polar organic polymer or a mixture of a polar organic polymers. By this treatment, the glass surface is modified in a direction towards lower polarity with the effect that it has lower attraction or adhesive forces towards hemoglobin and other proteinaceous macromolecules and other components of the blood or biological fluid where a polar attraction otherwises would tend to bind these compounds to the glass. The work required to separate reversibly the interface between two phases, work of adhesion, can be expressed in the following equation:

$$\gamma = \gamma A + \gamma B - \gamma AB$$

wherein $\gamma A$ is the surface tension of phase A, $\gamma B$ is the surface tension of phase B, and $\gamma AB$ is the interfacial tension between the two phases.

Thus, e.g. if A is a glass surface and B is a protein molecule, the $\gamma A$ and $\gamma B$ will both have a high value, whereas $\gamma AB$ will have a relatively low value, thus resulting in a high work of adhesion, $\gamma$. By modifying the glass surface, so that we have a modified glass surface, $\gamma A$ will be lower, $\gamma B$ will retain its value, and $\gamma AB$ may be the same or higher, thus resulting in a lower work of adhesion, $\gamma$.

By utilizing this principle, the binding of a highly adhesive blood macromolecule such as hemoglobin is reduced relative to the binding of histamine. With respect to histamine binding to the modified glass, the sum of the surface tension contributions for the modified glass surface and the histamine may well be lower than in the case of the non-modified glass, but on the other hand, the interfacial tension $\gamma AB$ will be lower so that the resulting work of adhesion $\gamma$ may well be substantially equal to that for the untreated glass.

Thus, the treatment of the surface of the inorganic histamine-binding material for the purpose of the present invention may be obtained by means of any agent which will result in a suitable reduction of the polarity or surface tension of the surface of the material, but whith retention of the capability of the glass to bind histamine for the determination.

Agents necessary for this purpose are, for example, polar polymers, that are close to the polar histamine molecule with respect to the so-called solubility parameters, thereby exhibiting a non-barrier effect with respect to histamine's access to the histamine-binding surface, i.e. in particular polymers containing heteroatoms such as oxygen or nitrogen, examples of such groups being hydroxy groups, carboxy groups, ester groups, carbonyl groups, ether groups and heterocyclic groups containing heteroatoms such as oxygen or nitrogen.

Without specifying wide limits for suitable polymers, it should be mentioned that the polymer should not have such a high molecular weight that it cannot be evenly distributed over the glass surface.

The polymer may be applied in any suitable manner from a liquid dispersion or solution or it may be polymerized in situ from monomers.

The polymers are not limited to homopolymers but may suitably and in certain cases advantageously be copolymers or mixtures of polymers or mixtures of polymers and copolymers. The decisive feature is in all cases that the polymer is capable of conferring a lower polarity or surface tension to the glass surface while retaining the essential histamine binding capacity.

The suitability of a polymer or copolymer or mixture of polymers and/or copolymers for the purpose of the invention may be determined by preliminary tests performed in accordance with known methods, such as contact angle measurements and tests of solubility parameters. The practical test in most cases is that the resulting treated glass surface should have, compared to the untreated glass surface, a reduced affinity to potentially interfering sample components while retaining the necessary histamine binding capacity.

The solubility parameters employed may suitably be those described in "Handbook of Solubility Parameters and other Cohesion Parameters", A. F. M. Barton, CRC Press (1983) (denoted hereafter ref. A), incorporated by reference herein, as pertinent. A useful model is the three-dimensional solubility parameter theory developed by Charles M. Hansen which is useful for predicting the capability of solvents or solvent mixtures to dissolve polymers. The three solubility parameters employed in this model are the so-called "dispersion", "polar", and "hydrogen-bonding" parameters ($\delta_D$, $\delta_P$ and $\delta_H$, respectively).

The solubility parameters for histamine may be calculated using a group-contribution method as described in ref. A., chapter 6.8, or may be determined empirically. The solubility parameters for the binder can likewise be determined by group-contribution methods (see ref. A, chapter 14.5), or empirically, or from data compilations (see e.g., ref. A, chapter 14.3). In the present context, this implies that the solubility parameters of the binder as interference-reducing agent should be close to those of the histamine.

The solubility coordinates of histamine in Hansen's three-dimensional coordinate system lie within the solubility parameter sphere of the binder. If the histamine solubility parameter position is not encompassed by the solubility parameter sphere of the binder, the binder will act as a barrier for histamine, thus preventing access of histamine to the histamine-binding material. Preferably, histamine is freely soluble in the binder.

Apart from exhibiting the properties described above, preferred binders as used according to the present invention should also exhibit surface tension low enough to substantially prevent adhesion of interfering sample components, such as proteins or other biological macromolecules. Relevant surface tension data can be found e.g., in "Polymer Interface and Adhesion", S. Wu, Marcel Dekker, New York and Basel (1982), incorporated by reference herein, as pertinent.

An aqueous suspension or dispersion of a vinyl acetate/ethylene copolymer stabilized with polyvinyl alcohol has been found to be an excellent polymer both for the treatment of the conglomerate surface as an interference-reducing agent as well as in the attachment of the glass fibers to each other forming the conglomerate and fix the conglomerate to the support in accordance with another of the aspects of the invention. Therefore, the use of such a suspension or dispersion is presently preferred and is illustrated in examples hereinafter.

When the above-described Hansen theory is applied to the preferred combination of histamine-binding material and binder according to the present invention, the theory does indeed predict that the solubility parameter position of histamine in the three-dimensional coordinate system is encompassed by the solubility parameter sphere of a vinylacetate-based copolymer of the type used, in other words that histamine should be able to migrate freely through a layer of such a binder deposited on a histamine-binding material. Preferably, the histamine-binding material is treated with an agent whose solubility parameter sphere encompasses the solubility parameter position of histamine.

The amount of polymer to be used in the treatment should be adapted to the particular inorganic material and the particular polymer used. In the cases where the same polymer or mixture of polymers is used to obtain both the interference-reducing (surface-modifying) effect and the binder-attachment effects, the amount will normally be higher than where surface modification is the only aim. However, there may be a gradual transition from a condition where a slight extent of surface modification has been obtained to a condition where a conglomerate of inorganic histamine-binding material has received such an amount of polymer that a major reason for the reduction of the interference of non-histamine components in the sample may be more related to modified spatial/steric conditions at or in the vicinity of the histamine-binding surfaces.

A preferred embodiment of the present invention in which glass microfibers are fixed in tray wells with the aid of a binder provides the advantage that the fibres are mechanically fixed to the wells and able to withstand the washing procedures necessary for the removal of the undesired blood components.

In a further aspect of the present invention, a method for the determination of histamine in a sample of whole blood may further comprise the provision of an agent capable of inducing histamine-release from cells sensitive to the agent such that said agent is present together with the conglomerate so that the sample is contacted with both the agent and the conglomerate. Such an agent may be an allergen, i.e. an antigen which gives rise to an allergic reaction in certain individuals. Examples of important and relevant allergens are allargens which normally are airborn and can therefore be inhaled, such as allergens in pollen of birch, grass and mugwort, allergens in horse, dog or cat dander, dust, mite allergens and mould fungus allergens. Allergens which can be present in foods and beverages, and may therefore be ingested, include allergens of cow milk, chicken egg, rye flour, wheat flour, oat meal, pork, beef, codfish, soybean, and green pea.

An important agent capable of inducing histamine-release from cells is anti-IgE.

It is clearly advantageous to incorporate an allergen in the same compartment as a conglomerate, since the user of the test-set is then freed from the necessity of acquiring and adding allergen extracts.

From the point of view of the shelf-life and handling, it is particularly advantageous to provide allergens in a substantially dry condition together with conglomerates. In a preferred embodiment of a test-set according to the present invention (vide infra) a carrier in the form of a well in a Microtiter tray incorporates dried standardized allergen extracts together with the conglomerate.

In a still further aspect of the present invention, a method for the determination of histamine in a sample of whole blood wherein an agent capable of inducing histamine-release from cells sensitive to the agent is present together with the conglomerate may further comprise the provision of an agent capable of enhancing the release of histamine from cells sensitive to the histamine release-inducing agent, such that the histamine release-enhancing agent is present together with the conglomerate and the histamine release-inducing agent.

The deliberate inclusion of a moderate background concentration of histamine is advantageous when employing a detection method such as that employed in a preferred embodiment of a method as disclosed in the invention, namely a fluorometric method, in that raising the base line level of fluorescence due to histamine considerably reduces the uncertainty in the determination of the lowest levels of histamine release from cells.

A further aspect of the invention comprises the use of special washing procedures employing media containing agents promoting the displacement of, or the degradation of, non-specifically bound blood components, thereby further facilitating the use of whole blood in the analysis.

Such agents may be selected from a group comprising agents influencing surface tension in the media employed, preferably surface active agents (surfactants), notably detergents. The detergent may be an anionic, a cationic, a switterionic or a non-ionic detergent, preferably a non-ionic detergent. Examples of suitable detergents are given below.

Table 2: Detergents

Anionic Detergents alkylsulfate salts, such as sodium laurylsulfate, triethanolammonium laurylsulfate, triethanolammonium cetylsulfate and triethanolammonium oleylsulfate, alkylsulfonate salts, such as "Hostapur SAF-60" [the latter being of the type $CH_3CH(R)SO_3^-$, $Na^+$; R=long-chain alkyl]

alkylbenzenesulfonate salts, such as sodium dodecylbenzenesulfonate.

Cationic Detergents quaternary ammonium salts, such as cetyltrimethylammonium bromide and "benzalkonium chloride" [the latter being a mixture of alkyldimethylbenzylammonium chlorides of the general formula $C_6H_5CH_2N(CH_3)_2(R)^+,Cl^-$, where $R=C_8-C_{18}$ alkyl].

Zwitterionic Detergents the "Sulfobetaines", "Lysolecithin", "Empigen BB", "Zwittergent 3-12" and "Zwittergent 3-14".

Non-Ionic Detergents alkylphenylpolyoxyethylene, including nonylphenylpolyoxyethylenes such as "Berol 09" and p-tert-octylphenylpolyoxyethylenes such as "Triton X-100", "Triton X-102", "Triton X-114" and "Triton X-165", polyoxyethylene alcohols, such as "Brij 35", "Brij 38", "Lipal 9LA", "Lipocol C-20", "Lauromacrogol 400" and "Cetomacrogol 1000", polyoxyethylene sorbitol esters, such as "Tween 80".

When appropriate, a mixture of different detergents may be employed.

A suitable agent may also be an enzyme which alters the structure of one or more of the interfering components so as to promote their displacement from the histamine-binding material. Such an enzyme may, for example, be a proteolytic enzyme degrading proteinaceous blood components into smaller fragments. Examples of commercially available "broad-spectrum" proteolytic enzymes are: "Alcalase", "Esperase", "Savinase", "Maxatase" and "Rapidase".

In another aspect, a detergent/enzyme combination of agents may be employed. A suitable combination of this type is "Biotrinon" (Bie & Berntsen, Denmark), containing the non-ionic detergent "Berol 09" and the protease "Alcalase" (vide supra). In the method as implemented at the present time it has been found advantageous to include a small quantity of "Renafix" (a detergent-preparation comprising both non-ionic and anionic detergents), in the detergent/ enzyme solution.

Samples subjected to the method of the invention may be biopsy samples. The biopsy material may be any material obtained from a human being or animal, provided that said material comprises cells capable of releasing histamine. The biopsy may be obtained from a tissue part of the respiratory system, in particular tracheobronchial tract, and lung tissue; the gastrointestinal tract; material from peritoneal or pleural cavities; or pathological tissue.

Often biopsy material obtained during an endoscopy procedure is employed, e.g. endoscopy of the gastrointestinal tracts such as the stomach, duodenum, and/or jejunum/ ileum. Furthermore, cells obtained via bronchoscopy may be examined.

The biopsy material should be kept under suitable conditions, i.e. kept in suitable media. A typical cell dispersion procedure is to cut the biopsy material into minor pieces and subjecting said pieces into medium containing e.g. collagenase, and subsequently incubating so as to obtain a preparation comprising dispersed cells. An example of a histamine-releasing cell-enriched preparation is a mast cell and/ or a basophilic leucocyte preparation.

The applicability of the method of the invention on human intestinal mast cells is shown by Nolte et al., Agents and Actions, Vol. 26 3/4 (1989), incorporated herein by reference.

Further aspects of the invention relate to a method and a test set for identifying or quantitating an agent capable of inducing release of histamine from histamine-containing cells. The method comprises incubating, in a medium, the agent with cells capable of releasing histamine into the medium when contacted with said agent, contacting the medium with a conglomerate which comprises (a) a material which is capable of binding histamine, and (b) a binder, such that at least part of the histamine in the sample is bound to the histamine-binding material;

determining the amount of histamine in the sample on the basis of the amount of histamine bound, correlating said bound histamine amount to standard values obtained for known amounts of the agent; and identifying or quantifying the agent.

Figures 1, 2, 3, 4, 5:
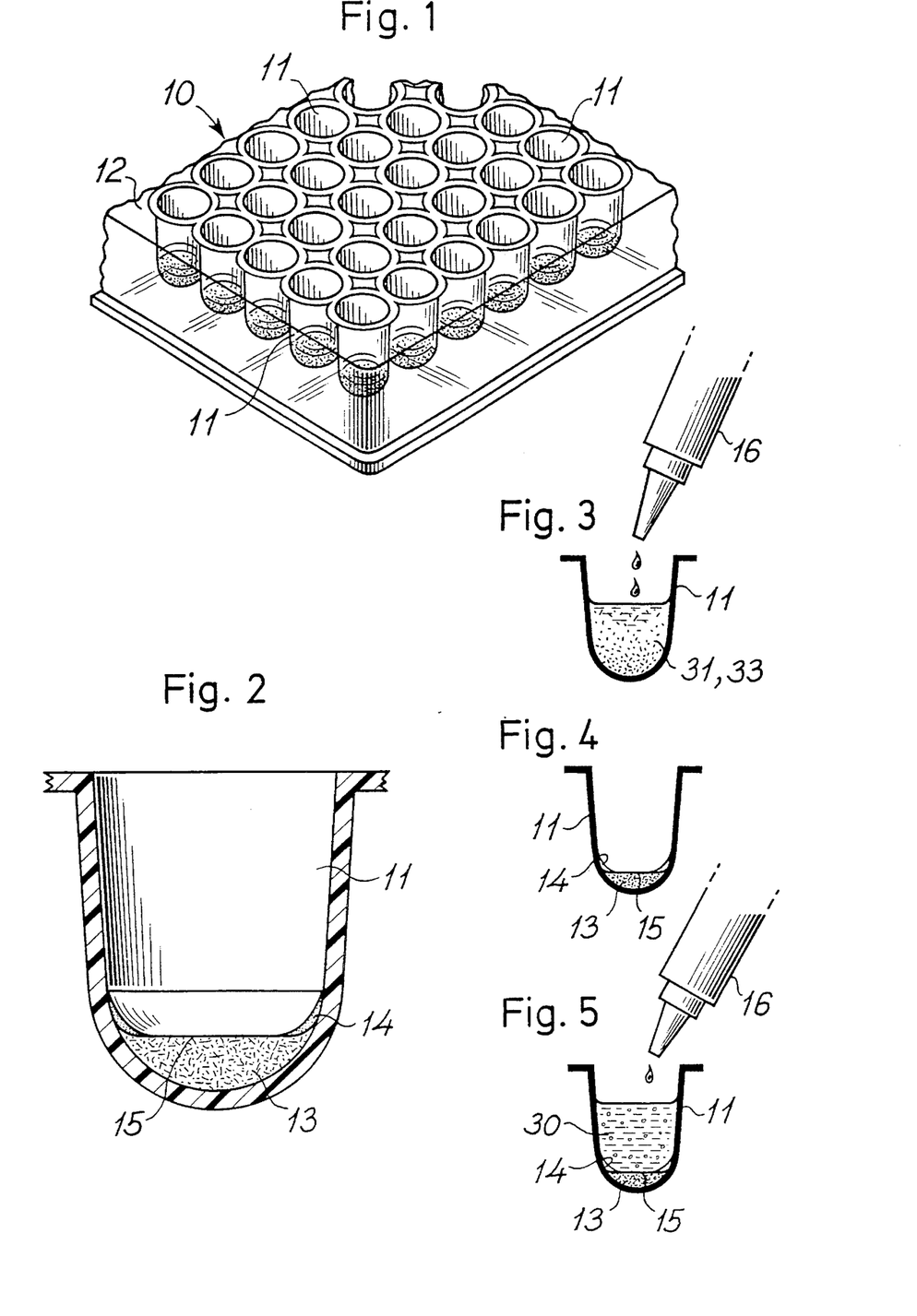

A commercial test set useful for this procedure is a set as illustrated, e.g., in FIG. 1, the wells in this embodiment of the test set being free from allergens.

Standardization procedures employing these aspects of the invention will provide simple and reproducible standardization of a wide range of allergens because they are based on what could be designated as a "miniature in vivo allergic reaction".

DETAILED DESCRIPTION OF THE DRAWINGS

FIG. 1 shows, in perspective, a part of a Microtiter tray 10 having wells 11 extending downward from an upper surface 12.

Each of the wells 11 contains at its bottom a fixed conglomerate comprising histamine-binding bodies such as will be explained in detail in connection with FIG. 2.

FIG. 2 shows a cross section of one of the wells 11 as shown in FIG. 1. A conglomerate 13 at the bottom of the well consists of bodies of histamine-binding material such as glass microfibers of a length between 2 and 20 µm and a thickness of between 0.3 and 2 µm bound by means of a binder such as a vinyl acetate/ethylene copolymer, applied from an aqueous suspension thereof. 14 designates a binder meniscus which is often found to be formed above the main part of the conglomerate, and 15 designates the upper surface of the conglomerate. The fibrous conglomerate, the preparation of which is performed e.g. as described in Example 1a–d, has a fiber concentration (or, otherwise expressed: porosity determined by a number of factors such as the size and the size-distribution of the microfibers in the conglomerates and the manner in which the conglomerate has been formed, such as explained and illustrated herein.

FIGS. 3–4 illustrate steps in the process of preparing the conglomerates at the bottom of the wells 11. In FIG. 3, a suspension comprising glass microfibers and binder such as a dispersed vinylacetate/ethylene copolymer binder as described above and illustrated in Example 1 is applied in a well 11 from a dispenser 16. The suspension is typically an aqueous suspension as described in Example 1. The presence of both the fibers and the dispersed microparticles of the binder is symbolized by the Nos. 31 and 33.

FIG. 4 illustrates the situation after the dispersion applied in FIG. 3 has been allowed to evaporate and to result in a structure corresponding to the one explained in connection with FIG. 2.

FIG. 5 illustrates an example of the introduction of a liquid distribution 30 (the solution) of a histamine release inducing agent such as an aqueous solution of an allergen in the well. After the introduction of the aqueous solution 30 the water is evaporated so as to leave a well comprising the conglomerate 13 with its upper surface 15 combined with the histamine release-inducing agent. As the histamine-inducing agent is thus applied from a liquid which is evaporated, the manner in which the histamine release-inducing agent such as an allergen would be placed in combination with the conglomerate 13 in the well will depend on various factors such as the chemical character of the allergen, the molecular size of the allergen, etc., but at any rate the histamine release-inducing agent should be arranged in such a manner in combination with a conglomerate that the sample will contact the allergen prior to or substantially simultaneously with its contact with the conglomerate. It should be understood, however, that the main feature of this aspect of the invention is not in which exact time wise sequence the sample will contact the allergen and the conglomerate but rather that the allergen thus is present in the wells prior to the introduction of the sample and is capable of inducing histamine release from cells in the sample (depending upon the reaction of the sample to the allergen) in such a manner that an amount of histamine representative of the released histamine becomes bound to the histamine-binding material of the conglomerate and can thus be determined by the method of the invention.

Figure 6:
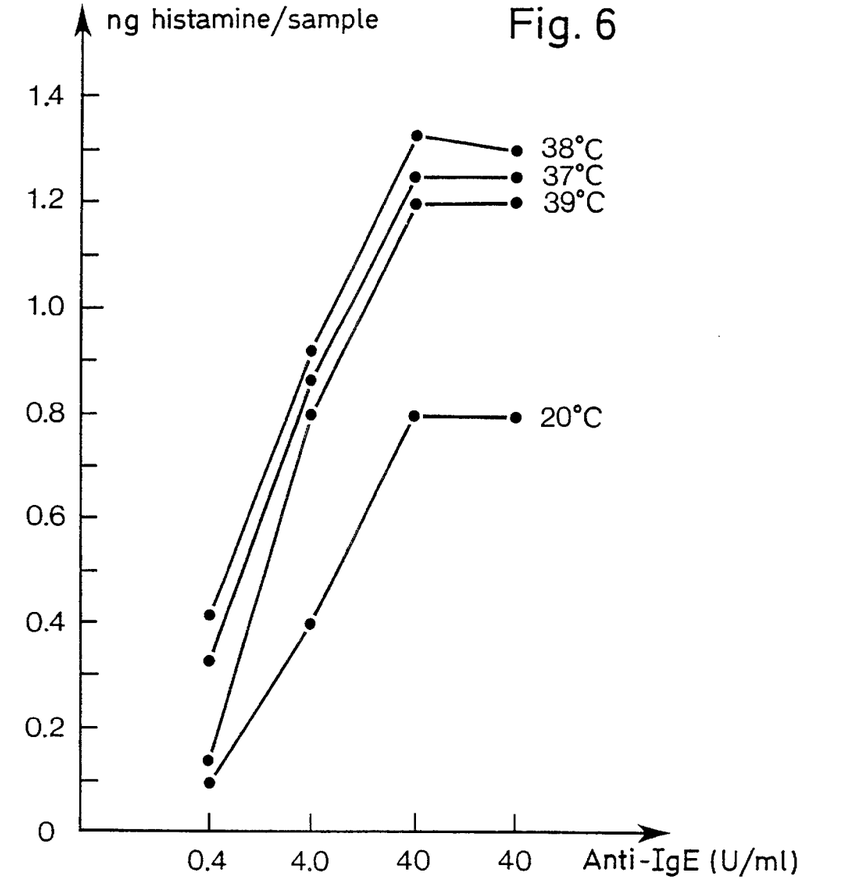
FIG. 6 shows plots illustrating the temperature variation of the amount of histamine released in a whole blood sample (measured in ng histamine per sample) as a function of concentration of anti-IgE; temperatures: 20°, 37°, 38° and 39° C.

FIG. 6 is discussed in Example 6.1.

Figure 7:
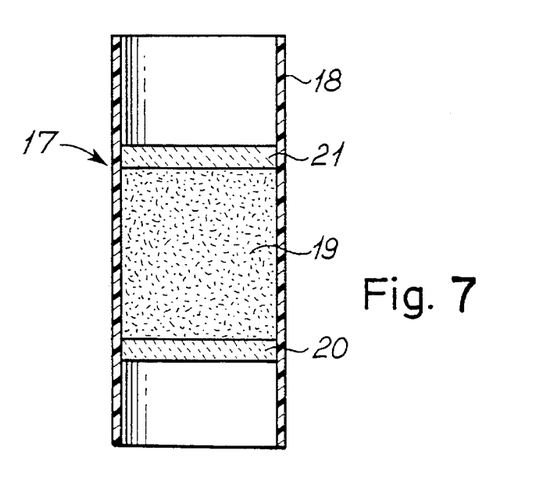
FIG. 7 shows a diagrammatic view of a test set in the form of a column.

FIG. 7 illustrates another embodiment of a test set useful for the method of the invention and comprising a container with contents (in its entirety designated 17). The container may be a cylindrically shaped container 18 such as a column packed with fixed or confined histamine-binding material. In a container column 18 made of a suitable material, such as polystyrene, a bed or layer 19 of bodies of a histamine-binding material, in particular particles or fibres made of silicon dioxide-based material, especially glass material, is arranged fixed or confined by means of a bottom filter 20 and optionally a top filter 21.

As an alternative, the histamine-binding bodies, especially in the form of particles such as powders, or fibers such as microfibers, especially prepared from glass material, may be present in the form of a conglomerate comprising a binder and said bodies. In a particular embodiment, the layer 19 may designate a layer comprising fibers which in themselves show no, or substantially no, histamine-binding capacity, but which act as a support for particles such as powders or fibers of histamine-binding material distributed in the fibrous mass constituted by the first mentioned fibers which have no or substantially no histamine-binding capacity. In this manner, histamine-binding materials which might in themselves have geometric properties which would not be optimal for the flow of a sample through the layer and/or which would not have a sufficient filter or distributing effect might be useful when combined with the fibers which act as support therefor.

The optional filter 21 at the top of the layer 19 may serve as a further confining boundary for the layer 19, and it may be provided, e.g. at the top thereof, with a material to which a sample of a body fluid or body tissue should be exposed prior to contact of the sample with the histamine-binding material, for example an allergen. In the embodiment shown in FIG. 8, the layer 19, whether consisting of one kind of bodies or a composite of two or more kinds of bodies as explained above may, if desired, also be present in the form of one or more conglomerates, in which a binder conglomerates the particles or fibers present.

It will be understood that the composition explained in connection with the layer 19 may also be useful in the layer 13 arranged in a well as explained and shown in connection with FIG. 2, that is, also such a layer might comprise "inactive fibers" which act as a support and/or distribution material for e.g. bodies of histamine-binding material, the bodies optionally being conglomerated with the fibrous material by means of a binder. If such a composite layer is prepared by sedimentation, the sedimentation rates of particles such as powder particles should be adapted to the sedimentation rate of the fibers so that the desired distribution of the powder in the fibrous masses is obtained, and/or fibers should be sedimented before the powder so that a fibrous layer is first formed whereupon powder and optionally further amounts of fiber are arranged. The result may then either be a subtantially homogenous distribution of the histamine-binding bodies in the fibrous mass, or bodies arranged subtantially in a layer or layers in the fibrous mass.

The container 17 may confine a volume of several milliliters, and for instance may be a tube with a diameter of several millimeters, or it may be a capillary tube, depending on the particular procedure employed.

EXAMPLE 1

Preparation of glass fiber coated Microtiter trays (batches of 200–400 trays)

a. Preparation of Glass Fiber Suspension

To obtain crushed glass microfibers, Whatman GF/B glass microfiber filter sheet (5 g) was cut into pieces of 2 cm×2 cm and milled in a Retch ball-mill operated in the following manner:

automatic discontinuous mode, i.e. 18 sec run in one direction, 5 sec stop, 18 sec run in the opposite direction, rotation speed 80% of max.

treatment time 5 min

A portion of 24 g of the crushed glass fibers (obtained by a total of 5 runs as above) was suspended in 1000 ml of freshly distilled water in a 1 liter brown glass bottle at ambient temperature.

The suspension was agitated thoroughly for 1 min and then transferred immediately to two 1000 ml glass beakers (500 ml in each; liquid height 8 cm in each beaker).

The crushed fibers were then allowed to sediment for 2 min at ambient temperature, after which the supernatant was transferred to a clean 1 liter brown glass bottle by careful decantation. This supernatant contains crushed fibers of dimensions from ca. 2 μm to ca. 20 μm.

A 15 ml aliquot of supernatant crushed glass fiber suspension prepared as above (hereafter called crushed glass fiber suspension) was evaporated to dryness in an oven at 95° C. The crushed glass fiber residue weighed 0.33 g, corresponding to a crushed glass fiber content in the suspension of 22 g per liter.

b. Preparation of Binder Dispersion

For this purpose a commercially available vinyl acetate/ethylene copolymer dispersion (Vinnapas-Dispersion EP 400; Wacker Chemie Danmark A/S, Denmark) was employed. The latter product has a dry matter content of ca. 55% (w/w) and a density of ca. 1.06 g/cm$^3$, the predominant emulsion particle size being ca. 0.8 μm (20° C.), Polyvinyl alcohol is incorporated as an emulsion stabilizer.

The latter dispersion was further diluted in freshly distilled water (100 mg copolymer per ml water) by thorough agitation at ambient temperature.

c. Preparation of Binder/Crushed Glass Fiber Dispersion 12.5 ml of binder dispersion prepared as above was added to 1000 ml of crushed glass fiber suspension and the mixture was agitated for 2 min.

600 ml of the resulting binder/crushed glass fiber dispersion was transferred to a 1000 ml glass beaker and stirred magnetically for at least 2 min before initiating the tray coating procedure, the stirring being such that gentle movement of the surface of the suspension was visible. Stirring was maintained throughout the dispersion dispensing stage of the tray coating procedure (see below).

d. Fixation in Microtiter Trays

A 12 channel peristaltic pump (Paxall; fitted with silicone rubber tubing: inner diameter 0.65 mm, outer diameter 2.45 mm, length 60 cm) was used to transfer 50 μl binder/crushed glass fiber dispersion to each of the wells of polystyrene Microtiter trays (Nunc, Denmark, 8×12 wells). The pump was operated in the following manner:

delivery adjusted to give 50 1 per well speed: setting 3 filling volume: setting 2

The pump was activated manually using a foot pedal.

The pumping system was equilibrated after 10 dosages. After filling 5 Microtiter trays, they were immediately placed in a Termaks oven (temperature 95°±2° C.) and dried overnight.

The trays were then removed from the oven and stored in plastic bags until the allergen coating procedure (shelf life: min. 6 months).

e. Preparation of Coating Dispersion

Optionally the trays prepared according to example 1.d. may be subject to a further coating. For this purpose a commercial available polyvinyl alcohol, W25/190, Wacker Chemie Danmark A/S, is prepared in a stock solution of 10% (w/v) and 60 μl stock solution is dispersed into 10 ml distilled water.

f. Coating of Microtiter Trays

50 μl coating dispersion prepared as above is applied to each of the wells of the microtiter trays to which the binder/crushed glass fiber conglomerate has been fixed according to 1.d.

The microtiter trays are then dried over night as for the fixation procedure.

EXAMPLE 2

PREINCUBATION WITH ALLERGENS

EXAMPLE 2.1

Inhalation Allergen Coating of the Glass Fiber Coated Trays.

Trays prepared as described in Example 1 were employed. The following solutions were prepared:

stock human serum albumin solution: 0.3 mg human serum albumin (SIGMA) per 100 ml distilled water;

working human serum albumin dilution (HSA): 180 µl stock human serum albumin solution was diluted with 100 ml distilled water (this solution was stored in a refrigerator);

stock histamine solution (100 mg/l): 100 mg histamine made up to 1 liter with distilled water working histamine solution (WHS) (5 mg/l): 250 µl stock solution was diluted to 5 ml with distilled water;

An anti-IgE standard (denoted AIS in the following) purchased from Behringwerke, Germany (400,000 U/ml) was used for the wells containing anti-IgE.

The Microtiter wells are designated as follows: horizontal rows: A–H, vertical columns: 1–12. Each well was filled with 25 µl of a solution prepared as outlined below, dispensed from a dosaging apparatus.

As an example a tray may be dispensed as follows.

Histamine standards:

| Well A1: | 210 µl WHS + 20790 µl HSA = 50 ng/ml |
| --- | --- |
| Well B1: | 5600 µl of soln. for A1 + 1400 µl HSA = 40 ng/ml |
| Well C1: | 4200 µl of soln. for A1 + 2800 µl HSA = 30 ng/ml |
| Well D1: | 2800 µl of soln. for A1 + 4200 µl HSA = 20 ng/ml |
| Well E1: | 1400 µl of soln. for A1 + 5600 µl HSA = 10 ng/ml |
| Well F1: | 0 µl of soln. for A1 + 7000 µl HSA = 0 ng/ml |
| Well G1: | 0 µl of soln. for A1 + 7000 µl HSA = 0 ng/ml |
| Well H1: | 1400 µl of soln. for A1 + 5600 µl HSA = 10 ng/ml |
| Well A2: | 2800 µl of soln. for A1 + 4200 µl HSA = 20 ng/ml |
| Well B2: | 4200 µl of soln. for A1 + 2800 µl HSA = 30 ng/ml |
| Well C2: | 5600 µl of soln. for A1 + 1400 µl HSA = 40 ng/ml |
| Well D2: | 210 µl of soln. for A1 + 20790 µl HSA = 50 ng/ml |

Anti-IgE standards:

| Well E2: | 225 µl AIS + 11250 µl HSA |
| --- | --- |
| Well F2: | 600 µl of soln. for E2 + 3150 µl HSA |
| Well G2: | 112 µl of soln. for E2 + 4388 µl HSA |
| Well H2: | 112 µl of soln. for E2 + 4388 µl HSA |
| Well A3: | 112 µl of soln. for E2 + 4388 µl HSA |

Inhalation allergen standards: Columns 3–12 (with the exception of well A3) (inhalation allergen extracts supplied by Pharmacia, Sweden: 100,000 BU/ml for birch, grass and mugwort, 10,000 BU/ml for all the others).

Column 3: birch (*Betula verrucosa*)
Column 4: grass (*Phleum pratense*)
Column 5: mugwort (*Ambrosia artemisifolia*)
Column 6: horse dander
Column 7: dog dander
Column 8: cat dander
Column 9: dust mite (*Dermatophagoides pteronyssinus*)
Column 10: dust mite (*Dermatophagoides farinae*)
Column 11: mould fungus (*Alternaria tenuis*)
Column 12: mould fungus (*Cladosporium herbarum*)

Row A and Row B (except well A3 in the case of birch):
for birch, grass and mugwort: 80 µl allergen extract+7920 µl HSA;
for all the other allergens: 800 µl allergen extract+7200 µHSA;
Row C: 840 µl of the soln. for A and B+2160 µl HSA
Row D: 240 µl of the soln. for A and B+2760 µl HSA
Row E: 101.5 µl of the soln. for A and B+4399 µl HSA
Row F: 870 µl of the soln. for A and B+2130 µl HSA
Row G: 234 µl of the soln. for A and B+2766 µl HSA
Row H: 67.5 of the soln. for A and B+2932.5 µl HSA After filling the wells, the trays were dried overnight in an oven at 37° C.

The trays were then tested as follows: The histamine standards in columns 1 and 2 in each of ten trays from each batch were checked by fluorometry (vide infra), and all the wells of three trays from the same batch were also checked fluorometrically, blood samples taken from three donors having known and well-characterized allergies being used for testing the inhalation allergen standards.

Finally, the trays were packed individually in gas-tight foil in a nitrogen atmosphere and batch-marked. Estimated shelf-life: ca. 6 months.

EXAMPLE 2.2

Food Allergen Coating of the Glass Fiber Coated Trays

Trays prepared as described in Example 1 were employed (batches of 60 trays). Apart from the food allergen extracts, the solutions were as described in Example 2.1.

The Microtiter wells are designated as described in Example 2.1. Each well was filled with 25 µl of a solution prepared as outlined below, dispensed from a dosaging apparatus.

Histamine standards: as in Example 2.1.

Anti-IgE standards: as in Example 2.1.

Food allergen standards: Columns 3–12 (with the exception of well A3) [food allergen extracts supplied by ALK, Denmark: 1:100 w/v for chicken egg, 1:20 w/v for all others].

Column 3: cow milk
Column 4: chicken egg
Column 5: rye flour
Column 6: wheat flour
Column 7: oatmeal
Column 8: pork
Column 9: beef
Column 10: codfish
Column 11: soya bean
Column 12: green pea Row A and Row B (except well A3 in the case of cow milk):
300 µl allergen extract+2700 µl HSA
Row C: 679 µl of the soln. for A and B+1750 µl HSA
Row D: 637 µl of the soln. for C+1750 µl HSA
Row E: 154 µl of the soln. for C+1750 µl HSA
Row F: 154 µl of the soln. for D+1750 µl HSA
Row G: 707 µl of the soln. for F+1750 µl HSA
Row H: 735 µl of the soln. for G+1750 µl HSA The trays were dried and tested, packed and batch-marked as described in Example 2.1. Coated trays prepared according to Example 1.f. may be preincubated analogously.

ANALYSIS OF HISTAMINE RELEASE

EXAMPLE 3 a. Source of Sample Material

Blood was drawn from each patient by venipuncture and collected in suitable plastic or glass tubes (e.g. "Venoject" tubes) containing a suitable anticoagulant, preferably heparin (as e.g. sodium or potassium heparinate), e.g. 0.5 ml of a 30 U heparin/ml solution so as to obtain 3 U heparin per ml blood when 5 ml blood was collected. Usually 5 ml were collected, however 2.5 ml provided enough sample material for testing for allergy to all the allergens in one tray. For testing for allergy to a single allergen, as little as 1 ml of blood was sufficient.

Blood samples were usually stored at 20°–25° C. (higher temperatures result in too rapid denaturation and deterioration of samples, and too low temperatures lead to precipitation). The samples could normally be sent by ordinary mail and were preferably analysed within 24 hours after sample obtainment, although satisfactory analyses could still be obtained after 48 hours.

b. Preparing Solutions and Trays to be used in the Analyses

Trays prepared as described in Examples 2.1 and 3.2 were employed.

The following solutions were prepared:
working human serum albumin (HSA) dilution: as in Example 2.1;
working histamine solution (WHS) (5 mg/l): as in Example 2.1
PIPES buffer: 3.02 g PIPES [piperazine-N,N'-bis(2-ethanesulfonic acid)], 19.05 g sodium acetate and 0.49 g potassium acetate, 20–21 ml 1M TRIS [tris(hydroxymethyl)aminomethane] solution (to give final pH 7.4), 600 µl 1M CaCl$_2$ and 1100 µl 1M MgCl$_2$ are made up to 1 liter with distilled water. This stock solution is kept in a refrigerator;
working buffer: to PIPES buffer was added, immediately prior to use, glucose (1 g per liter PIPES buffer), HSA (1.6 ml per liter PIPES buffer) and heparin solution (LEO, sodium heparinate, 5000 IU per ml; 3 ml per liter PIPES buffer) (the heparin solution was stored in a refrigerator);
intermediate histamine-buffer solution (IHBS) (100 ng/ml): 100 µl WHS was diluted to 5 ml with working buffer;
blank histamine-buffer solution (HBS) (10 ng/ml): 5 ml intermediate histamine-buffer solution was diluted with 45 ml working buffer;
detergent/enzyme solution: 5 mg "Biotrinon" (Bie & Berntsen, Denmark) was dissolved in 10 ml distilled water containing 25 µl "Renafix" (Perfection A/S, Tåstrup, Denmark);
OPT solution: 5 mg o-phthaldialdehyde (analytical grade, Fluka) was dissolved in 500 µl methanol, and this solution was diluted to 10 ml with 0.05M NaOH; final pH 12.56;
0.59% perchloric acid; pH 1.16.

25 µl HBS were introduced (using an "Easy Dispenser") into each well, i.e. 0.25 ng histamine per well, and the tray and the blood sample were then placed in an oven at 38° C. for ½ hour.

25 µl blood were than pipetted (using an Eppendorph pipette) into each well, and the tray was then covered and incubated for 1 hour at 38° C. It was then washed five times with deionized water in an immuno-washer apparatus.

50 µl detergent/enzyme solution was pipetted into each well (Volac dispensing equipment), and the tray was then covered and incubated for ½ hour at 38° C.

The tray was then washed five times as described above.

75 µl OPT soultion were added ("Easy Dispenser") to each well, after which the tray was allowed to stand for 10 min at room temperature.

75 µl perchloric acid solution were then introduced ("Easy Dispenser") into each well, and the tray was allowed to stand in the dark for 5 min at room temperature.

The fluorescence intensity in the wells was measured at 455 nm using a Perkin Elmer fluorometer. The histamine concentrations obtained for the patients samples were correlated to the standard histamine curves and the values obtained from the anti-IgE containing wells. The amount of histamine release provoked by the various allergens was calculated, and the amounts divided, e.g., into 4 groups: negative reaction, weak positive reaction, medium positive reaction and strong positive reaction.

ANALYSIS FOR ALLERGY TO BEE AND WASP VENOM ALLERGEN

EXAMPLE 4

Trays prepared as described in example 1.d. were employed. For analysis using these allergens, the histamine standards, anti-IgE standards and allergen standards were introduced into the appropriate wells immediately before incubation of the trays at 38° C. for 1 hour (as in Example 3). The following solutions were employed:
intermediate histamine-buffer solution (IHBS) (100 ng/ml): as in Example 3.
working buffer: as in Example 3.
anti-IgE standard (AIS): as in Examples 2.1 and 2.2.

The Microtiter wells are designated as described in Example 2.1. Each well was filled with 25 µl of a solution prepared as outlined below, dispensed from a dosaging apparatus.

Histamine standards:
Wells A1,B1,C1,A2,B2,C2: 5000 µl IMBS+5000 µl working buffer
Wells D1,D2: 800 µl of soln. for A1-C2+200 µl working buffer
Wells E1,E2: 600 µl of soln. for A1-C2+400 µl working buffer
Wells F1, F2: 400 µl of soln. for A1-C2+600 µl working buffer
Wells G1,G2: 200 µl of soln. for A1-C2+800 µl working buffer
Wells H1,H2: 1000 µl working buffer
Anti-IgE standards:
Wells A3,B3,A4,B4: 61 µl AIS+3000 µl working buffer
Wells C3,C4: 425 µl of soln. for A3-B4+1500 µl working buffer
Wells D3,D4: 79 µl of soln. for A3-B4+1500 µl working buffer
Wells E3,E4: 375 µl of soln. for D3,D4+1500 µl working buffer
Wells F3,F4: 69 µl of soln. for D3,D4+1500 µl working buffer
Wells G3,G4: 79 µl of soln. for E3,E4+1500 µl working buffer
Wells H3,H4: 379 µl of soln. for G3,G4+1500 µl working buffer
Bee/wasp venom allergen standards: Columns 5 and 6: bee venom allergen; Columns 7 and 8: wasp venom allergen.

The allergenic strength of the supplied extracts (Pharmacia, Denmark (100 µl/mg)] varied, and the highest dilution concentration (to be used in Wells A and B) for a new batch of allergen extract was therefore established by testing against blood from non-allergic test subjects. As before, 25 μl aliquots of solutions prepared as outlined below were added to the appropriate wells; the following data are typical:

Wells A,B: 5 μl allergen extract+995 μl working buffer
Wells C: 97 μl of soln. for A,B+250 μl working buffer
Wells D: 91 μl of soln. for C+250 μl working buffer
Wells E: 22 μl of soln. for C+250 μl working buffer
Wells F: 22 μl of soln. for D+250 μl working buffer
Wells G: 101 μl of soln. for F+250 μl working buffer
Wells H: 105 μl of soln. for G+250 μl working buffer The blood sample and the prepared tray were then incubated at 38° C. for ½ hour, after which 25 μl blood were added to each well and the analysis was carried out as described in Example 3.

EXAMPLE 5

Measurement of Histamine Added to Whole Blood

Non-coated microtiter trays, i.e. trays prepared according to example 1.d. and trays coated as described in Example 1.f. were added 25 μl heparinized whole blood not previously treated in any way.

25 μl working Pipes buffer with or without 50 ng histamine/ml, were applied to each well to provide samples and blanks, respectively, and the trays were incubated in an oven at 38° C. for half an hour. Analysis for histamine was carried out fluorometrically as described in Example 3.

Table 3 shows the means and standard deviations of 4 batch runs (1,2,3 and 4) each comprising histamine concentrations of 20 samples and 20 blanks expressed in fluorescence units for coated and non-coated trays. Also, the grand mean and standard error of mean are shown for both sets of trays.

It is seen that the fluorescence of blanks in coated trays (162±10 fluorescence units) are reduced significantly, i.e. 44%, compared to non-coated trays (233±22).

Also, the net-values (193±16), show a significant increase, i.e. 64%, compared to non-coated trays (118±22).

This comparison example simulates a detection of the presence of histamine in whole blood as a result of an allergic reaction and clearly shows the advantages of the invention.

To illustrate the possibility of using either washed blood or whole blood in the histamine release test blood was washed according to example 2 in U.S. Pat. No. 4,550,085.

The washed blood and the whole blood from one patient were then tested for histamine release using allergen coated trays prepared according to example 1.d. and 2.

Table 4 shows the measured histamine release (ng histamine/ml blood. It is clear that histamine released because of an allergic reaction in whole blood or in washed blood can be measured by the method according to the invention.

Furthermore, the whole blood and the washed blood generally showed consistent allergy reactions, it being understood that the detection limit for a "positive" reaction is 15 ng histamine/ml blood.

TABLE 4

Measured Histamine Release (ng Histamine/ml Blood) using Allergen Coated Trays and whole/washed Blood

| Allergen | Preparation | Allergen Concentration (BU/ml) | | | | | |
|---|---|---|---|---|---|---|---|
| | | 500 | 140 | 40 | 11.3 | 3.3 | 0.9 |
| Birch | Whole | 11 | 11 | 15 | 5 | 6 | 0 |
| | Washed | 0 | 0 | 0 | 1 | 0 | 0 |
| Grass | Whole | 16 | 2 | 5 | 8 | 13 | 9 |
| | Washed | 0 | 0 | 0 | 1 | 0 | 0 |
| Mugworth | Whole | 9 | 7 | 5 | 12 | 1 | 0 |
| | Washed | 1 | 0 | 0 | 0 | 0 | 0 |
| Horse | Whole | 7 | 1 | 9 | 7 | 8 | 0 |
| | Washed | 9 | 1 | 0 | 0 | 0 | 0 |
| Dog | Whole | 36 | 13 | 41 | 30 | 14 | 0 |
| | Washed | 46 | 32 | 12 | 5 | 0 | 0 |
| Cat | Whole | 32 | 39 | 41 | 30 | 14 | 0 |
| | Washed | 23 | 26 | 25 | 38 | 29 | 21 |
| Dust Mite | Whole | 9 | 0 | 0 | 0 | 0 | 0 |
| Derm Pteronyssinus | Washed | 10 | 6 | 2 | 3 | 0 | 0 |
| Alternaria | Whole | 14 | 9 | 8 | 0 | 3 | 0 |
| | Washed | 4 | 3 | 2 | 2 | 0 | 0 |
| Cladosporium | Whole | 0 | 0 | 0 | 0 | 0 | 0 |
| | Washed | 1 | 1 | 0 | 1 | 0 | 0 |

TABLE 3 shows the results of histamine measurements of samples and blanks expressed in fluorescence units for non-coated and coated trays in 4 batch runs.

| Tray | | Batch run no. | | | | Means of batches |
|---|---|---|---|---|---|---|
| | | 1 | 2 | 3 | 4 | |
| Non-coated (n = 20) | Sample* | 363 ± 19 | 335 ± 7 | 350 ± 20 | 355 ± 20 | 351 ± 12 |
| | Blank** | 237 ± 2 | 214 ± 10 | 263 ± 10 | 218 ± 14 | 233 ± 22 |
| | Net*** | 126 | 121 | 86 | 137 | 118 ± 22 |
| Coated (n = 20) | Sample | 349 ± 12 | 360 ± 20 | 347 ± 11 | 364 ± 10 | 355 ± 8 |
| | Blank | 164 ± 10 | 149 ± 8 | 172 ± 1 | 163 ± 12 | 162 ± 10 |
| | Net | 184 | 201 | 175 | 211 | 193 ± 16 |

*Samples comprise 25 μl heparinized whole blood + 25 μl working Pipes buffer with 50 ng histamine/ml.
**Blanks comprise 25 μl heparinized whole blood + 25 μl working Pipes buffer.
***Net equals sample minus blank

EXAMPLE 6

Measured Histamine Released Because of an Allergic Reaction in Whole or Washed Blood

ANALYSIS OF TEMPERATURE INFLUENCE ON HISTAMINE RELEASE

EXAMPLE 7.1

In one investigation, blood samples from 17 patients were each divided into 2 aliquots, each of which was analysed essentially as described in Example 4, except that one of each pair of aliquots was preheated for ½ hour at 37° C. prior to establishing the contact with allergens and/or anti-IgE, while the other aliquot was kept at ambient temperature (ca. 20°–23° C.). For 12 of the 17 samples, an increase in histamine release of approximately 20% was observed. The values for the remaining samples were either unchanged or only slightly improved.

EXAMPLE 7.2

A blood sample from a patient exhibiting adequate response to anti-IgE was divided into 4 aliquots. Prior to analysis, the sample aliquots were incubated for ½ hour at 20° C., 37° C., 38° C. and 39° C., respectively. 25 µl of each aliquot were then transferred to glass fiber coated Microtiter tray wells (4 trays, prepared as in Example 2.1) containing anti-IgE (incorporated in the trays in the same manner as described in Examples 2.1 and 2.2), and the trays were then incubated for 1 hour at the same temperatures as employed for incubation of the sample aliquots.

Histamine release was determined fluorometrically by comparison with histamine standards also incorporated in the trays (cf. Example 3). The results showed that 38° C. was the optimum temperature, the histamine release obtained at 38° C. being 10% greater than at 37° C.

The results are shown in FIG. 6.

EXAMPLE 8

Effect of the polar polymer

To obtain an impression of the effect of the polar polymer with respect to reducing interference with the analysis caused by blood components, the following simple experiment was performed:

192 discs of Whatman GF/B glass fiber filter sheet of diameter 7 mm were stamped out from an intact sheet and introduced into the bottom of the wells of two Microtiter trays of the type shown in FIG. 1 (vide infra). 50 µl of binder dispersion prepared as described in Example 1 were introduced into each well of one of the trays, whereas 50 µl of distilled water were introduced into each well of the other tray. Both trays were then dried as described in Example 1.d. 25 µl of background histamine buffer and 25 µl of whole blood were then introduced into all the wells of both trays, and the trays were then incubated for 1 hour at 38° C. in an oven, as in Example 3.

The trays were then treated with detergent/enzyme solution and washed with deionized water as described in Example 3, after which it was immediately apparent with the naked eye that the glass fiber discs in the tray without binder retained considerably more blood colour than the glass fiber discs in the other tray, indicating that the ability of at least some hemoglobin-carrying components present in whole blood to bind to the glass fibers in the presence of binder is appreciably reduced relative to the binding ability of the fibers in the absence of binder.

EXAMPLE 9

Coating effect on allergene

Coated and non-coated trays as described in Example 5 were provided with allergen as described in Example 2 and compared using blood from a multiallergic patient.

Table 5 shows that the coating does not affect the allergens since significant histamine release, i.e. histamine release ≧15 ng histamine/ml whole blood, is observed at the same allergen concentrations for similar allergens in both types of trays.

TABLE 5

Coating effect on allergens

| Allergen | Tray | Allergen Concentration (BU/ml) | | | | | |
|---|---|---|---|---|---|---|---|
| | | 500 | 140 | 40 | 11.3 | 3.3 | 0.9 |
| Birch | Non-coated | 34 | 30 | 38 | 28 | 28 | 26 |
| | Coated | 45 | 45 | 42 | 37 | 31 | 16 |
| Grass | Non-coated | 40 | 38 | 34 | 30 | 30 | 24 |
| | Coated | 54 | 55 | 51 | 46 | 31 | 23 |
| Mugworth | Non-coated | 20 | 12 | 4 | 0 | 0 | 0 |
| | Coated | 15 | 8 | 8 | 0 | 0 | 0 |
| Horse | Non-coated | 6 | 3 | 0 | 0 | 0 | 0 |
| | Coated | 6 | 0 | 0 | 0 | 0 | 0 |
| Dog | Non-coated | 24 | 12 | 7 | 3 | 0 | 0 |
| | Coated | 23 | 27 | 4 | 0 | 0 | 0 |
| Cat | Non-coated | 22 | 15 | 11 | 7 | 2 | 0 |
| | Coated | 36 | 25 | 22 | 13 | 5 | 0 |
| Alternaria | Non-coated | 20 | 25 | 20 | 15 | 9 | 3 |
| | Coated | 37 | 36 | 34 | 22 | 14 | 4 |

EXAMPLE 10

Comparison of Stored and Newly Prepared Allergen Coated Glass Microfibre Trays

Allergen coating of coated vinyl acetate/ethylene copolymer coated glass microfibre trays were performed according to Example 1.d. and 2 providing "dry allergens".

Pipetting of freshly diluted allergens on to copolymer coated glass microfibre trays were also performed according to Example 2 thus providing "wet allergens".

Assay using the two types of allergen coated glass microfibre trays was performed according to Example 3 using blood from two allergic patients.

Tables 6 and 7 show that the "dry allergens" and the "wet allergens" provide comparable results, and that significant histamine release, i.e. histamine release ≧15 ng histamine/ml whole blood, is observed at the same allergen concentrations in both types of allergen preparations for similar allergens for both patients.

Thus the allergens in the allergen coated glass microfibre tray preserves their ability to induce allergic reactions.

TABLE 6

Stored (Dry) and Newly Prepared (Wet) Allergen Coated Glass Microfibre Trays (Patient No. 1)

| Allergen | Preparation | Allergen Concentration (BU/ml) | | | | | |
|---|---|---|---|---|---|---|---|
| | | 500 | 140 | 40 | 11.3 | 3.3 | 0.9 |
| Birch | Wet | 0 | 1 | 0 | 0 | 0 | 0 |
| | Dry | 0 | 0 | 1 | 0 | 0 | 0 |
| Grass | Wet | 42 | 36 | 0 | 0 | 0 | 0 |
| | Dry | 43 | 28 | 4 | 0 | 0 | 0 |
| Mugworth | Wet | 8 | 0 | 0 | 0 | 0 | 0 |
| | Dry | 5 | 0 | 0 | 0 | 0 | 0 |
| Horse | Wet | 33 | 33 | 27 | 18 | 10 | 5 |
| | Dry | 32 | 35 | 23 | 15 | 12 | 0 |

TABLE 6-continued

Stored (Dry) and Newly Prepared (Wet) Allergen Coated
Glass Microfibre Trays
(Patient No. 1)

| Allergen | Prepa-ration | Allergen Concentration (BU/ml) | | | | | |
|---|---|---|---|---|---|---|---|
| | | 500 | 140 | 40 | 11.3 | 3.3 | 0.9 |
| Dog | Wet | 24 | 25 | 12 | 1 | 0 | 0 |
| | Dry | 26 | 25 | 10 | 0 | 0 | 0 |
| Cat | Wet | 28 | 26 | 7 | 6 | 6 | 0 |
| | Dry | 29 | 27 | 9 | 8 | 0 | 0 |
| Dust Mite | Wet | 27 | 32 | 14 | 2 | 0 | 0 |
| Derm Pteronyssinus | Dry | 27 | 36 | 18 | 1 | 0 | 0 |
| Alternaria | Wet | 32 | 16 | 0 | 0 | 0 | 0 |
| | Dry | 34 | 14 | 0 | 0 | 0 | 0 |
| Cladosporium | Wet | 34 | 23 | 2 | 4 | 0 | 0 |
| | Dry | 38 | 27 | 0 | 0 | 0 | 0 |

TABLE 7

Stored (Dry) and Newly Prepared (Wet) Allergen Coated
Glass Microfibre Trays
(Patient No. 2)

| Allergen | Prepa-ration | Allergen Concentration (BU/ml) | | | | | |
|---|---|---|---|---|---|---|---|
| | | 500 | 140 | 40 | 11.3 | 3.3 | 0.9 |
| Birch | Wet | 8 | 0 | 0 | 0 | 0 | 0 |
| | Dry | 2 | 0 | 0 | 0 | 0 | 0 |
| Grass | Wet | 34 | 27 | 10 | 2 | 0 | 0 |
| | Dry | 36 | 33 | 15 | 11 | 0 | 0 |
| Mugworth | Wet | 3 | 4 | 2 | 0 | 0 | 0 |
| | Dry | 0 | 0 | 0 | 1 | 0 | 0 |
| Horse | Wet | 5 | 2 | 0 | 1 | 0 | 0 |
| | Dry | 0 | 2 | 0 | 1 | 0 | 0 |
| Dog | Wet | 0 | 0 | 0 | 0 | 0 | 0 |
| | Dry | 7 | 1 | 0 | 0 | 0 | 0 |
| Cat | Wet | 0 | 0 | 0 | 0 | 0 | 0 |
| | Dry | 0 | 0 | 0 | 0 | 0 | 0 |
| Dust Mite | Wet | 0 | 0 | 0 | 0 | 0 | 0 |
| Derm Pteronyssinus | Dry | 0 | 0 | 0 | 0 | 0 | 0 |
| Alternaria | Wet | 0 | 0 | 0 | 0 | 0 | 0 |
| | Dry | 3 | 6 | 0 | 0 | 0 | 0 |
| Cladosporium | Wet | 0 | 0 | 0 | 0 | 0 | 0 |
| | Dry | 6 | 0 | 0 | 2 | 0 | 0 |

EXAMPLE 11

Binding of Histamine to Different Types of Glasses

The binding of histamine to different types of glass was investigated by column chromatography.

Methods:

1. 200 mg of glass was filled in a column (inner diameter=1 cm) with phosphate buffer. The glasses that were used and their composition are shown in table 1.
2. The column was washed for 15 min. with phosphate buffer. The flow rate was 50 ml/min. This flow rate was used throughout the experiment.
3. A solution of histamine (2 mg/ml) in phosphate buffer was pumped through the column for 20 min.
4. Then the column was washed with phosphate buffer for about 15 min.
5. The histamine that has bound to the glass was eluated with 0.59% $HClO_4$. The acid solution was pumped through the column for 10 min. The eluate was collected from the time when the flow was changed from the phosphate buffer to the acid solution. Every 2 minutes a new sample was collected ending up with 5 samples of the eluate.
6. The samples were analysed for histamine with ophthaldialdehyde with the procedure described in example 3b. The results are shown in table 8.

TABLE 8

| Binding of Histamine to Different Types of Glasses | | | | |
|---|---|---|---|---|
| Type of glass | GF/B | CPG-10 | 108A | 106Q |
| Histamine (ng/ml) | 160 | 206 | 67 | 127 |

It is clear from these results that it is possible to use different types of glasses as histamine binding material besides the Whatman®GF/B glass fiber.

EXAMPLE 12

Investigation of Histamiine Binding to Polymer Coated Microfibers as a Function of the Hansen Solubility Parameters for the Polymer The solubility parameters for histamine were calculated by Charles M. Hansen according to the group contribution method (Ref. A, op.cit.) and were as follows:

$\delta_D=17.3$  $\delta_P=7.5$  $\delta_H=12.2$

The solubility parameters for various polymers were determined empirically as suggested by Charles M. Hansen.
The following results were obtained:

| Ethylene/vinylacetat copolymer latex | $\delta_D$ | $\delta_P$ | $\delta_H$ | R | dist. histamin | RED* |
|---|---|---|---|---|---|---|
| Vinnapas EP 400 | 17.2 | 10.6 | 7.2 | 9.6 | 5.89 | 0.613 |
| SBR-latex**** | 20.3 | 9.3 | 3.9 | 8.7 | 10.4 | 1.195 |
| Dow 460 | | | | | | |
| Acryl latex: | | | | | | |
| Rhoplex N580** | 16.2 | 7.6 | 10.2 | 10.6 | 2.97 | 0.281 |
| Rhoplex 1031** | 19.3 | 10.7 | 6.7 | 12.4 | 7.97 | 0.642 |
| Polysar PL 6779*** | 19.3 | 14.1 | 3.9 | 14.8 | 11.33 | 0.766 |

*Relative Energy Distance (Hansen nomenclature), RED:

$$RED = \frac{dist.\ histamine}{R}, wherein?$$

$$dist.\ histamine = \sqrt{(2\Delta\delta_D)^2 + \Delta\delta_P^2 + \Delta\delta_H^2}?$$

The $\Delta\delta$ values represent the difference between the respective $\delta$-values for histamine and the polymer.
R = the radius of the solubility parameter sphere for the polymer
For RED <1 the histamine parameter position is encompassed by the solubility parameter sphere
For RED >1 histamine is outside the sphere
**Supplied by Rohm & Haas, no data available
***Supplied by Polysar Nederland B.V. According to the supplier it is a modified acrylic ester copolymer latex in the form of a milky white liquid having a viscosity of 0.09 PanS, a density of 1060 kg/m³, a boiling point of 100° C. and a pH in concentrated form of 5.1.
****Styrene/Butadiene/Rubber Latex supplied by Dow Chemical The histamine binding properties to glass microfibers coated with the above polymers as described in Example 1a–f were determined using Vinnapas EP400 (Example 1.d.) as a control.

In consistence with the theory based on the Hansen parameters the SBR late having an RED>1 prevented the histamine from binding to the glass microfibres.

The results are reported in Table 9 below:

TABLE 9

Histamine measurement (in fluorescence units) on acrylate coated glass microfibre

|  | Rhoplex N580 | Rhoplex N1031 | Polysar PL6779 | Control** |
|---|---|---|---|---|
| Sample* | 489 | 526 | 406 | 519 |
| Blank | 203 | 215 | 217 | 228 |
| Net | 286 | 311 | 279 | 287 |

*The histamine concentration in the sample was 125 ng/ml
**Non-coated microfibre trays prepared according to example 1.d.

The above results clearly show that the acrylate polymers, the solubility parameter sphere of which encompasses the parameter position of histamine, bring about a histamine binding which is comparable and even superior to the control and also to the results reported for coated trays in table 3.

These results confirm that the Hansen parameter theory is applicable in the selection of applicable binders for use in accordance with the present invention.

We claim:

1. In a diagnostic test device for use in an assay for histamine comprising a plurality of crushed glass microfibers which binds histamine and which are deposited onto a carrier, the improvement which comprises that the crushed glass microfibers have been conglomerated by a binder which reduces the affinity of the conglomerated crushed glass microfibers towards interfering components in a sample while their histamine-binding capacity is substantially retained; said binder being a polar organic polymer having a solubility parameter sphere substantially encompassing the solubility parameters for histamine.

2. The test device according to claim 1, wherein a binder is used which reduces the polarity or surface tension of the surface of the microfibers.

3. The diagnostic test device according to claim 1, wherein the crushed glass microfibers comprise a soda-lime glass or a borosilicate glass material.

4. The diagnostic test device according to claim 1, wherein the polar organic polymer comprises a polymer containing heteroatoms selected from the group consisting of oxygen and nitrogen atoms.

5. The diagnostic test device according to claim 1 wherein the polar organic polymer is selected from the group consisting of polyvinyl acetate, a vinyl acetate/ethylene copolymer, and polyvinyl alcohol.

6. The diagnostic test device according to claim 1, additionally comprising an agent which induces the release of histamine from cells such that cells brought into contact with the conglomerate of crushed glass microfibers will also be brought in contact with the agent.

7. The diagnostic test device according to claim 6, wherein the histamine release-inducing agent is an allergen.

8. The diagnostic test device according to claim 6, wherein the histamine release inducing agent is anti-IgE.

9. The diagnostic test device according to claim 1, wherein said device is a microtiter tray having individual wells, and wherein the conglomerated crushed glass microfibers are fixed within said wells.

10. The diagnostic test device according to claim 6, wherein said device is a microtiter tray having individual wells, and wherein said conglomerates are fixed within said wells, and wherein at least one of said wells additionally contains an agent which induces the release of histamine.

11. The diagnostic test device according to claim 1, wherein the length of said crushed glass microfibers is about 0.1 to about 200 μm.

12. The diagnostic test device according to claim 6, wherein the length of said crushed glass microfibers is about 0.1 to about 200 μm.

13. In a method for preparing a diagnostic test device for use in determination of histamine, wherein crushed glass microfibers which bind histamine and are suspended in a liquid are deposited and fixed onto a carrier, the improvement which comprises mixing the crushed glass microfibers with a binder distributed in the liquid, said binder being a polar organic polymer having a solubility parameter sphere substantially encompassing the solubility parameter for histamine; and drying the resulting mixture to obtain a solid conglomerate deposited and fixed onto said carrier.

14. The method of claim 13, wherein the length of said crushed glass microfibers is about 0.1 to about 200 μm.

\* \* \* \* \*

UNITED STATES PATENT AND TRADEMARK OFFICE
CERTIFICATE OF CORRECTION

PATENT NO. : 5,468,650
DATED : November 21, 1995
INVENTOR(S) : Per Stahl SKOV and Ole-Christian BJARNO It is certified that error appears in the above-indentified patent and that said Letters Patent is hereby corrected as shown below:

Title page, [54] Title of Invention, change "CLASS" to --GLASS--.

Title page, [73] Assignee: change "A/S Lundbeck Export Division Ltd., Copenhagen, Denmark" to --Allergifonden af 1981, Herlev, Denmark--.

Title page, add
--[30] FOREIGN APPLICATION PRIORITY DATA
Aug. 11, 1988 [DK] Denmark..................4510/88
Aug. 12, 1988 [DK] Denmark..................4551/88--.

Column 1, line 1, change "CLASS" to --GLASS--.

Signed and Sealed this

Twelfth Day of November, 1996

Attest:

BRUCE LEHMAN

*Attesting Officer*    *Commissioner of Patents and Trademarks*